(12) United States Patent
Zhong

(10) Patent No.: US 12,257,004 B2
(45) Date of Patent: Mar. 25, 2025

(54) METHODS AND SYSTEMS FOR CATHETER NAVIGATION

(71) Applicant: SHANGHAI UNITED IMAGING HEALTHCARE CO., LTD., Shanghai (CN)

(72) Inventor: Can Zhong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 198 days.

(21) Appl. No.: 17/930,406

(22) Filed: Sep. 7, 2022

(65) Prior Publication Data
US 2023/0073925 A1 Mar. 9, 2023

(30) Foreign Application Priority Data
Sep. 7, 2021 (CN) .......................... 202111044581.5

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/105* (2016.02)

(58) Field of Classification Search
CPC ...... A61B 2034/105; A61B 2034/2065; A61B 34/10; A61B 34/20
See application file for complete search history.

(56) References Cited

U.S. PATENT DOCUMENTS

| | | |
|---|---|---|
| 2005/0249327 A1 | 11/2005 | Wink et al. |
| 2006/0235671 A1 | 10/2006 | Kirchberg et al. |
| 2013/0211245 A1 | 8/2013 | Vembar et al. |
| 2016/0029981 A1 | 2/2016 | Van Dijk et al. |
| 2018/0330484 A1 | 11/2018 | Bauer et al. |
| 2019/0239961 A1 | 8/2019 | Birenbaum et al. |
| 2019/0350516 A1 | 11/2019 | Shen et al. |
| 2019/0350657 A1 | 11/2019 | Tolkowsky |
| 2020/0242767 A1 | 7/2020 | Zhao et al. |
| 2023/0181144 A1 | 6/2023 | Sun et al. |

FOREIGN PATENT DOCUMENTS

| | | |
|---|---|---|
| CN | 1931097 A | 3/2007 |
| CN | 101574266 A | 11/2009 |
| CN | 101849843 A | 10/2010 |
| CN | 102196768 A | 9/2011 |

(Continued)

OTHER PUBLICATIONS

The Extended European Search Report in European Application No. 22194417.6 mailed on Jan. 17, 2023, 10 pages.

(Continued)

*Primary Examiner* — Michael T Rozanski
(74) *Attorney, Agent, or Firm* — METIS IP LLC

(57) ABSTRACT

Methods and systems for catheter navigation are provided. The method may include obtaining at least one real-time image associated with a subject, the at least one real-time image including a catheter at least partially inside the subject; determining spatial position information associated with the catheter based on the at least one real-time image; and directing a display device to configure a virtual object corresponding to the catheter in a reference image associated with the subject based on the spatial position information.

19 Claims, 9 Drawing Sheets

(56) References Cited

FOREIGN PATENT DOCUMENTS

| CN | 103356155 | A | 10/2013 |
| CN | 110473297 | A | 11/2019 |
| CN | 111882510 | A | 11/2020 |
| CN | 112515767 | A | 3/2021 |
| CN | 112741692 | A | 5/2021 |
| EP | 2366448 | A1 | 9/2011 |
| JP | 2007151606 | A | 6/2007 |
| JP | 2009022733 | A | 2/2009 |

OTHER PUBLICATIONS

Yuan, Feiniu et al., Automatic Navigation for Virtual Endoscope, Space Medicine & Medical Engineering, 16(3):201-205, 2003.
Cui, Xiwen et al., Image-Guided Arthroscopic Surgery Based on Virtual Endoscopic Technology, Chinese Journal of Biomedical Engineering, 38(5): 558-565, 2019.

400

---

Obtaining at least one real-time image associated with a subject, the at least one real-time image including a catheter at least partially inside the subject
410

↓

Determining spatial position information associated with the catheter based on the at least one real-time image
420

↓

Directing a display device to configure a virtual object corresponding to the catheter in a reference image associated with the subject based on the spatial position information
430

FIG. 4

METHODS AND SYSTEMS FOR CATHETER NAVIGATION

CROSS-REFERENCE TO RELATED APPLICATIONS

This application claims priority of Chinese Patent Application No. 202111044581.5, filed on Sep. 7, 2021, the contents of which are entirely incorporated herein by reference.

TECHNICAL FIELD

The present disclosure relates to the field of medical technology, in particular, to methods and systems for catheter navigation.

BACKGROUND

In some examinations, surgeries, or treatments, it is necessary to place a catheter (or a guide wire) into a living body and guide the catheter to move in the body to assist in the procedure of the examinations, surgeries, or treatments. However, the doctor needs to repeatedly observe real-time images of the catheter in different directions to obtain the desired reference information, and the obtained reference information is generally inaccurate. Therefore, it is desirable to provide improved methods and systems for catheter navigation to provide accurate reference information conveniently and efficiently.

SUMMARY

One or more embodiments of the present disclosure provide a system for catheter navigation. The system may include at least one storage medium including a set of instructions, and at least one processor in communication with the at least one storage medium, wherein when executing the set of instructions, the at least one processor may be directed to cause the system to perform the following operations. At least one real-time image associated with a subject may be obtained, the at least one real-time image may include a catheter at least partially inside the subject, spatial position information associated with the catheter may be determined based on the at least one real-time image, and a display device may be directed to configure a virtual object corresponding to the catheter in a reference image associated with the subject based on the spatial position information.

One or more embodiments of the present disclosure provide a method for catheter navigation. The method may include the following operations. At least one real-time image associated with a subject may be obtained, the at least one real-time image may include a catheter at least partially inside the subject, spatial position information associated with the catheter may be determined based on the at least one real-time image, and a display device may be directed to configure a virtual object corresponding to the catheter in a reference image associated with the subject based on the spatial position information.

One or more embodiments of the present disclosure further provide a non-transitory computer readable medium, comprising executable instructions that, when executed by at least one processor, direct the at least one processor to perform a method, the method may include the following operations. At least one real-time image associated with a subject may be obtained, the at least one real-time image may include a catheter at least partially inside the subject, spatial position information associated with the catheter may be determined based on the at least one real-time image, and a display device may be directed to configure a virtual object corresponding to the catheter in a reference image associated with the subject based on the spatial position information.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further describable in terms of exemplary embodiments. These exemplary embodiments are describable in detail with reference to the drawings. These embodiments are non-limiting exemplary embodiments, in which like reference numerals represent similar structures throughout the several views of the drawings, and wherein:

FIG. 4 is a flowchart illustrating an exemplary process for catheter navigation according to some embodiments of the present disclosure;

DETAILED DESCRIPTION

Figure 1:
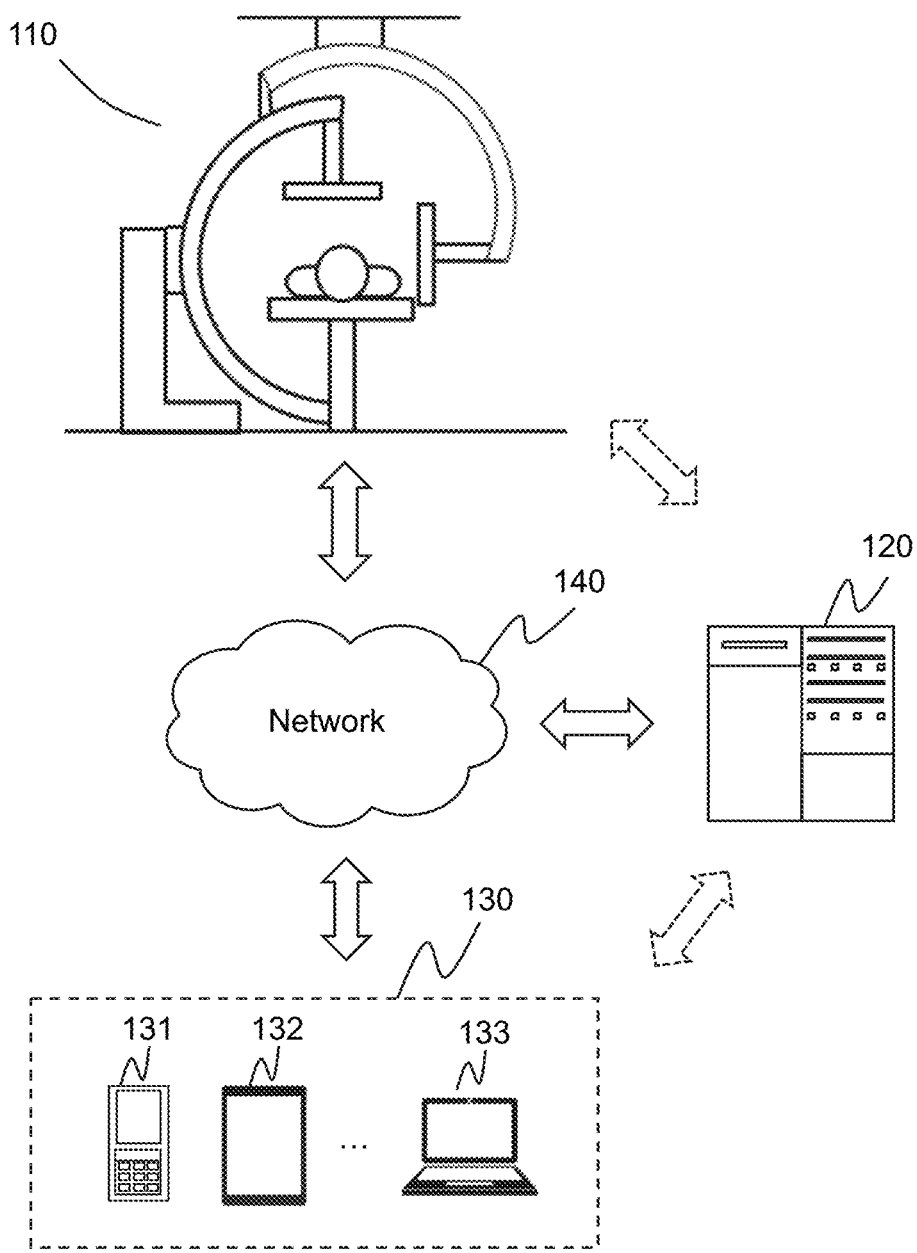
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been describable at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assemblies of different levels in ascending order. However, the terms may be displaced by other expressions if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the present disclosure, the subject may include a biological object and/or a non-biological object. The biological object may be a human being, an animal, a plant, or a specific portion, organ, and/or tissue thereof. For example, the subject may include the head, the neck, the thorax, the heart, the stomach, a vessel, a soft tissue, a tumor, a nodule, or the like, or any combination thereof. In some embodiments, the subject may be a man-made composition of organic and/or inorganic matters that are with or without life. The terms "object" and "subject" are used interchangeably in the present disclosure.

In the present disclosure, the term "image" may refer to a two-dimensional (2D) image, a three-dimensional (3D) image, or a four-dimensional (4D) image (e.g., a time series of 3D images). In some embodiments, the term "image" may refer to an image of a region (e.g., a region of interest (ROI)) of a subject. In some embodiment, the image may be a medical image, an optical image, etc.

As aspect of the present disclosure provides methods and systems for catheter navigation. The system may obtain at least one real-time image associated with a subject including a catheter at least partially inside the subject and determine spatial position information associated with the catheter based on the at least one real-time image. Further, the system may direct a display device to configure a virtual object corresponding to the catheter in a reference image (e.g., a 3D image) associated with the subject based on the spatial position information. According to the systems and methods of the present disclosure, the spatial position information of the catheter can be accurately determined based on the at least one real-time image, and the virtual object corresponding to the catheter configured in the reference image based on the spatial position information can provide accurate, intuitive, and convenient reference information for an operation (e.g., an examination, a surgery, a treatment) performed on the subject.

FIG. 1 is a schematic diagram illustrating an exemplary medical system according to some embodiments of the present disclosure. As shown in FIG. 1, the medical system 100 may include an acquisition device 110, a processing device 120, a terminal device 130, and a network 140. In some embodiments, the components of the medical system 100 may be directly connected with each other or via a network 140.

The acquisition device 110 may be used to obtain image data of a subject. In some embodiments, the acquisition device 110 may obtain real-time images (e.g., real-time images during the procedure of an examination, a surgery, a treatment, etc.) associated with the subject. In some embodiments, the acquisition device 110 may obtain a reference image (e.g., a reference image prior to an examination, a surgery, a treatment, etc.) associated with the subject. For example, taking the examination, the surgery, or the treatment relating to vessels as an example, the acquisition device 110 may obtain real-time vessel images or reference vessel images.

In some embodiments, the acquisition device 110 may include a Digital Subtraction Angiography (DSA) device. In some embodiments, the acquisition device 110 may include a single C-arm vascular machine (also referred to as a single-C vascular machine), a double C-arm vascular machine (also referred to as a double-C vascular machine), a U-arm vascular machine (also referred to as a U-shaped vascular machine), a G-arm vascular machine (also referred to as G-type vascular machine), or the like, or any combination thereof.

In some embodiments, the acquisition device 110 may include a Magnetic Resonance (MR) scanning device, a Computed Tomography (CT) scanning device, a Positron Emission Tomography (PET) scanning device, a Positron Emission Tomography-Computed Tomography (PET-CT) scanning device, or the like, or any combination thereof.

In some embodiments, the acquisition device 110 may obtain image data and generate corresponding images. In some embodiments, the acquisition device 110 may send the acquired image data to the processing device 120 via the network 140.

The processing device 120 may process information acquired from one or more other components (e.g., the acquisition device 110, the terminal device 130) of the medical system 100. In some embodiments, the processing device 120 may generate corresponding images based on the image data obtained by the acquisition device 110. In some embodiments, the processing device 120 may determine spatial position information associated with a catheter based on at least one real-time image associated with the subject obtained by the acquisition device 110.

In some embodiments, the processing device 120 may be a single server or a server group. The server group may be centralized or distributed. In some embodiments, the processing device 120 may be local or remote. For example, the processing device 120 may access information stored in the acquisition device and/or the terminal device 130 via the network 140. As another example, the processing device 120 may be directly connected to the acquisition device 110 and/or the terminal device 130. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components illustrated in FIG. 2.

The terminal device 130 may display information and/or interact with a user. In some embodiments, the terminal device 130 may configure a virtual object corresponding to the catheter in a reference image associated with the subject based on an instruction of the processing device 120 and display corresponding reference information associated with the catheter. In some embodiments, the terminal device 130 may receive user instructions (e.g., power on, power off, start scanning, abort scanning, stop scanning, configure parameters, reconstruct images, image registration).

In some embodiments, the terminal device 130 may include a mobile device 131, a tablet computer 132, a laptop computer 133, or the like, or any combination thereof. In some embodiments, the terminal device 130 may be externally connected or integrated with a display device. In some embodiments, the display device may include a Cathode Ray Tube display (CRT), a Light Emitting Diode display (LED), a Liquid Crystal Display (LCD), an Organic Light Emitting Semiconductor Display (OLESD), or the like, or any combination thereof.

In some embodiments, the terminal device 130 and the processing device 120 may be integrated as a single device. In some embodiments, all or part of the functions of the terminal device 130 and the processing device 120 may be implemented by a same device. In some embodiments, the terminal device 130 may be part of processing device 120.

The network 140 may include any suitable network that can facilitate the exchange of information and/or data for the medical system 100. In some embodiments, one or more components (e.g., the acquisition device 110, the processing device 120, the terminal device 130) of medical system 100 may communicate information and/or data with one or more other components of the medical system 100 via the network 140. For example, the terminal device 130 may obtain image data from the acquisition device 110 via the network 140. As another example, the processing device 120 may transmit instructions (e.g., a display instruction, a configuration instruction) to the terminal device 130 via the network 140. As a further example, the acquisition device 110 may obtain user instruction(s) from the terminal device 130 via the network 140.

In some embodiments, the network 140 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network (VPN), a satellite network, a telephone network, routers, hubs, switches, server computers, and/or any combination thereof. In some embodiments, the network 140 may include one or more network access points. For example, the network 140 may include wired and/or wireless network access points such as base stations and/or internet exchange points through which one or more components of the medical system 100 may be connected to the network 140 to exchange data and/or information.

In some embodiments, the medical system 100 may also include a storage device (not shown). The storage device may store data, instructions, and/or any other information. In some embodiments, the storage device may store data acquired from one or more components (e.g., the acquisition device 110, the processing device 120, the terminal device 130) of medical system 100. In some embodiments, the storage device may store data and/or instructions that the processing device 120 may execute or use to perform exemplary methods described in the present disclosure. In some embodiments, the storage device may include a mass storage device, a removable storage device, a volatile read-and-write memory, a read-only memory (ROM), or the like, or any combination thereof. In some embodiments, the storage device may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device may be connected to the network 140 to communicate with one or more other components (e.g., the acquisition device 110, the processing device 120, the terminal device 130) of the medical system 100. One or more components of the medical system 100 may access the data and/or instructions stored in the storage device via the network 140. In some embodiments, the storage device may be directly connected to or communicate with one or more other components (e.g., the acquisition device 110, the processing device 120, the terminal device 130) of the medical system 100. In some embodiments, the storage device may be part of the processing device 120 or the terminal device 130.

It should be noted that the above description regarding the medical system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical system 100 may include one or more additional components and/or one or more components of the medical system 100 described above may be omitted. Additionally or alternatively, two or more components of the medical system 100 may be integrated into a single component. A component of the medical system 100 may be implemented on two or more sub-components.

Figure 2:
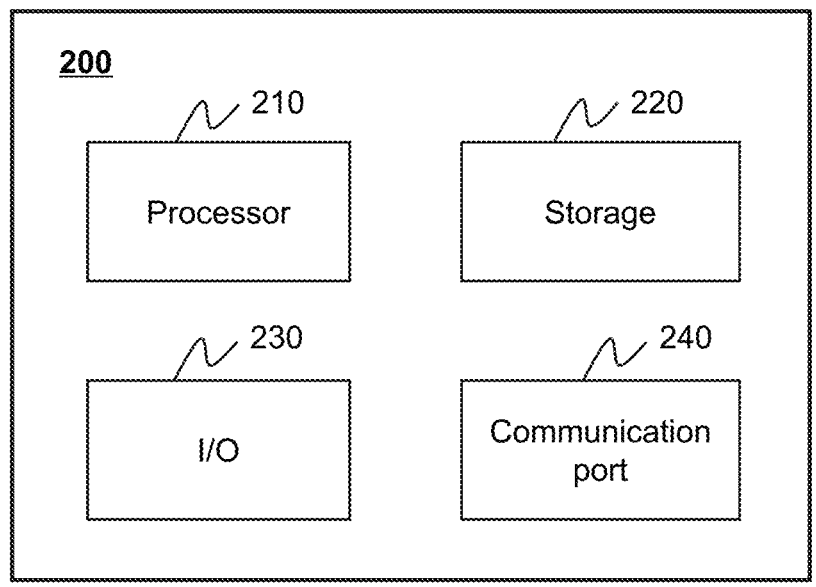
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. As illustrated in FIG. 2, the computing device 200 may include a processor 210, a storage 220, an input/output (I/O) 230, and a communication port 240. In some embodiments, the processing device 120 may be implemented on the computing device 200.

The processor 210 may execute computer instructions (program code) and, when executing the instructions, cause the processing device 120 to perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may process data and/or images acquired from the acquisition device 110, the terminal device 130, the storage device, and/or any other components of the medical system 100. For example, the processor 210 may obtain image data from the acquisition device 110.

In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method operations that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information acquired from the acquisition device 110, the terminal device 130, or any other components of the medical system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc.

In some embodiments, the storage 220 may store one or more programs and/or instructions to perform exemplary methods described in the present disclosure. For example, the storage 220 may store a program (e.g., in the form of computer-executable instructions) for the processing device 120 for catheter navigation.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 140) to facilitate data communications. The communication port 240 may establish connections between the processing device 120 and the acquisition device 110 and/or the terminal device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
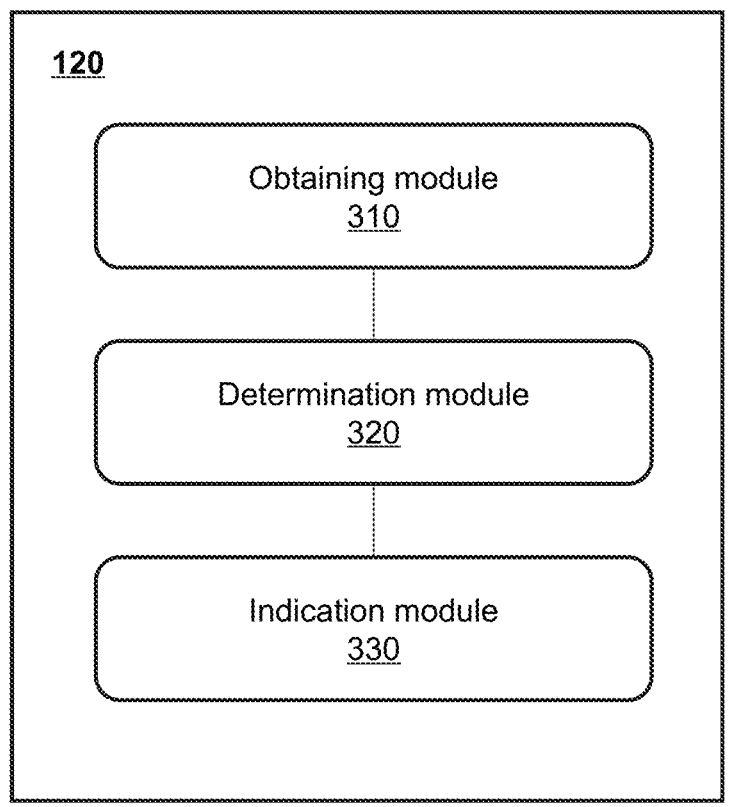
FIG. 3 is a block diagram illustrating an exemplary processing device according to some embodiments of the present disclosure.

FIG. 3 is a block diagram illustrating an exemplary processing device according to some embodiments of the present disclosure. As illustrated in FIG. 3, the processing device 120 may include an obtaining module 310, a determination module 320, and an indication module 330.

The obtaining module 310 may be configured to obtain at least one real-time image associated with a subject. In some embodiments, the at least one real-time image may include a catheter at least partially inside the subject.

The determination module 320 may be configured to determine spatial position information associated with the catheter based on the at least one real-time image.

The indication module 330 may be configured to direct a display device to configure a virtual object corresponding to the catheter in a reference image associated with the subject based on the spatial position information.

More detailed descriptions of the modules of the processing device 120 may be found in elsewhere of the present disclosure, for example, FIG. 4 and the descriptions thereof.

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 120 may include one or more other modules and/or one or more modules described above may be omitted. Additionally or alternatively, two or more modules may be integrated into a single module and/or a module may be divided into two or more units. However, those variations and modifications also fall within the scope of the present disclosure.

FIG. 4 is a flowchart illustrating an exemplary process for catheter navigation according to some embodiments of the present disclosure. In some embodiments, process 400 may be executed by the medical system 100. For example, the process 400 may be implemented as a set of instructions stored in a storage device. In some embodiments, the processing device 120 (e.g., the processor 210 of the computing device 200 and/or one or more modules illustrated in FIG. 3) may execute the set of instructions and may accordingly be directed to perform the process 400. The operations of the illustrated process presented below are intended to be illustrative. In some embodiments, the process 400 may be accomplished with one or more additional operations not described and/or without one or more of the operations discussed. Additionally, the order of the operations of process 400 illustrated in FIG. 4 and described below is not intended to be limiting.

In 410, the processing device 120 (e.g., the obtaining module 310) may obtain at least one real-time image associated with a subject.

As used herein, the subject may refer to a tube or a cavity within an organism. In some embodiments, the tube may include a vessel, a trachea, a gastric tube, a urinary tube, a fallopian tube, an intestinal tract, or the like, or any combination thereof. In some embodiments, the cavity may include a cranial cavity, a nasal cavity, a laryngeal cavity, a ventricle, a thoracic cavity, an abdominal cavity, a pelvic cavity, or the like, or any combination thereof. In some embodiments, the subject may also refer to a tissue, an organ, a bone, or the like, or any combination thereof.

In some embodiments, during the procedure of an examination, a surgery, or a treatment (also can be collectively referred to as an "operation") associated with the subject, the guidance of the procedure of the examination, the surgery, or the treatment may be accomplished through a catheter (or a guide wire). Accordingly, the at least one real-time image associated with the subject may at least include a catheter (or a guide wire) partially inside the subject, for example, a catheter partially located inside a vessel.

In the present disclosure, a "real-time image" may refer to an image acquired during the procedure of the examination, the surgery, or the treatment. Multiple "real-time images" may be acquired at the same point in time or at different points during a period of the examination, the surgery, or the treatment.

In some embodiments, the at least one real-time image may include a two-dimensional image. In some embodiments, the at least one real-time image may include a three-dimensional image or a four-dimensional image.

In some embodiments, the at least one real-time image may include real-time images acquired under at least two acquisition angles. For example, the at least one real-time image may include real-time two-dimensional images acquired under at least two acquisition angles. In some embodiments, the at least one real-time image may include a first real-time image acquired under a first acquisition angle and a second real-time image acquired under a second acquisition angle. For example, the at least one real-time image may include a first real-time two-dimensional image acquired under a first acquisition angle and a second real-time two-dimensional image acquired under a second acquisition angle.

In some embodiments, at least one real-time image may be obtained by multiple acquisition devices. In some embodiments, at least one real-time image may be obtained by multiple acquisition units of a single acquisition device. In some embodiments, at least one real-time image may be acquired by a single acquisition device (or single acquisition unit) under different acquisition angles.

Figure 5A:
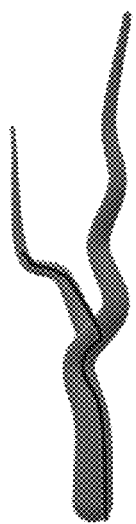
FIG. 5A and FIG. 5B are schematic diagrams illustrating real-time images of a vessel acquired under different acquisition angles according to some embodiments of the present disclosure.
Figure 5B:

In some embodiments, at least one real-time image may be obtained by a double C-arm acquisition device. The double C-arm acquisition device has two C-arms, and each C-arm may be provided with an acquisition unit (hereinafter referred to as a first acquisition unit and a second acquisition unit) with a specific acquisition angle. Accordingly, the double C-arm acquisition device may simultaneously acquire two real-time images at different acquisition angles. For example, FIG. 5A and FIG. 5B show exemplary real-time images of a vessel including a portion of a catheter located therein acquired by a double-C vascular machine under different acquisition angles.

In some embodiments, the at least one real-time image may be obtained by a single C-arm acquisition device. In this case, a gantry of the single-C-arm acquisition device may be controlled to reciprocate (e.g., swing) within a preset angle range (e.g., ±2°, ±3°, ±5°, ±8°, ±10°, ±15°), accordingly, multiple real-time images under different acquisition angles within a preset angle range may be acquired in a short time interval. In some embodiments, in order to ensure the accuracy of positioning, the image acquisition frequency may be set to be not lower than a moving speed of the catheter. For example, it is assumed that the catheter is moving at 30 frames per second or slower, the image acquisition frequency may be set as 30 frames per second. In some embodiments, in order to quickly acquire multiple real-time images and ensure the accuracy of positioning, the preset angle range should not be set too large (e.g., less than or equal to a range of ±15°).

In 420, the processing device 120 (e.g., the determination module 320) may determine spatial position information associated with the catheter based on the at least one real-time image.

In some embodiments, the spatial position information associated with the catheter may include position point information and/or direction information (or orientation information) of the catheter. In some embodiments, the position point information of the catheter may include coordinates (e.g., coordinates in the world coordinate system, coordinates in an image coordinate system) of a vertex of a front end of the catheter, coordinates of multiple reference points within a certain range of the front end of the catheter, coordinates of any point on a centerline of the catheter, coordinates of any point on the catheter, or the like, or any combination thereof. In some embodiments, the direction information of the catheter may include an orientation of the front end of the catheter, an angle between the front end of the catheter and any coordinate axis, or the like, or any combination thereof.

In some embodiments, as described in connection with operation 410, the at least one real-time image may include real-time images acquired under at least two acquisition angles. Accordingly, the determination module 320 may determine the spatial position information associated with the catheter based at least in part on the acquisition angles of the real-time images. For example, the determination module 320 may determine position information (also referred to as "position information" in image domain) associated with the catheter under the at least two acquisition angles based on the real-images. Further, the determination module 320 may determine reference spatial position information (e.g., coordinates of any point on a centerline of the catheter) associated with at least a portion of the catheter based on the position information under the at least two acquisition angles. Furthermore, the determination module 320 may determine position point information and/or direction information of a vertex of a front end of the catheter based on the reference spatial position information (e.g., coordinates of any point on the centerline of the catheter) associated with the catheter.

In some embodiments, as described in connection with operation 410, the at least one real-time image may include a first real-time image acquired under a first acquisition angle and a second real-time image acquired under a second acquisition angle. Accordingly, the determination module 320 may determine the spatial position information associated with the catheter based at least in part on the first acquisition angle and the second acquisition angle. For example, the determination module 320 may determine first position information associated with the catheter under the first acquisition angle and determine second position information associated with the catheter under the second acquisition angle. Further, the determination module 320 may determine reference spatial position information (e.g., coordinates of any point on a centerline of the catheter) associated with at least a portion of the catheter based on the first position information and the second position information. Furthermore, the determination module 320 may determine position point information and/or direction information of a vertex of a front end of the catheter based on the reference spatial position information (e.g., coordinates of any point on the centerline of the catheter) associated with the catheter.

Figure 6:
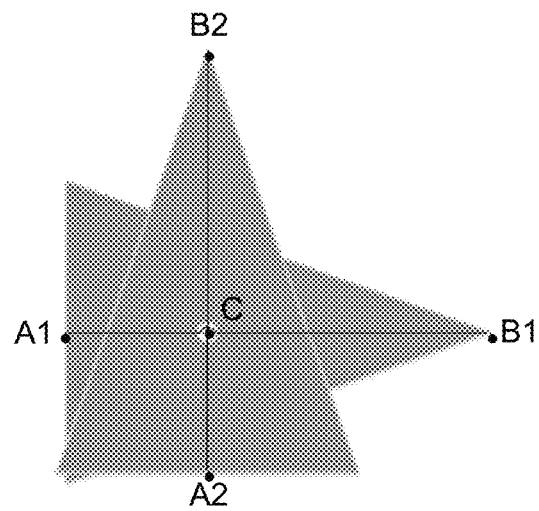
FIG. 6 is a schematic diagram illustrating an exemplary process for determining spatial position information of a catheter according to some embodiments of the present disclosure.

Merely by way of example, as shown in FIG. 6, the determination module 320 may determine a first point (e.g., point A1 shown in FIG. 6) associated with the catheter in the first real-time image, and determine a first line based on the first point and a first reference point (e.g., a focus B1 of a tube of the first acquisition unit shown in FIG. 6) associated with the acquisition of the first real-time image. For example, the first line may be a line connecting the first point and the first reference point. Similarly, the determination module 320 may determine a second point (e.g., point A2 shown in FIG. 6) associated with the catheter in the second real-time image, and determine a second line based on the second point and a second reference point (e.g., a focus B2 of a tube of the second acquisition unit shown in FIG. 6) associated with the acquisition of the second real-time image. For example, the second line may be a line connecting the second point and the second reference point.

In some embodiments, the first point and the second point may be imaging points of a certain actual position point (e.g., a point located on a surface or interior of the catheter, any predefined point on the catheter) associated with the catheter in the corresponding real-time images respectively. Accordingly, the first line and the second line are corresponding projection lines of the first point and the second point. Correspondingly, the intersection (e.g., point C shown in FIG. 6) of the first line and the second line is the actual position point associated with the catheter. Further, as shown in FIG. 6, the determination module 320 may determine the spatial position information of the actual position point based on the first line and the second line. For example, the determination module 320 may calculate coordinates of the intersection of a straight line equation corresponding to the first line and a straight line equation corresponding to the second line to obtain spatial coordinates of the actual position point associated with catheter. Furthermore, the determination module 320 may determine spatial coordinates of multiple actual position points on the catheter. In some embodiments, in order to simplify the calculation, the catheter may be regarded as a curve. In this way, a curve fitting may be performed based on the spatial coordinates of multiple actual position points associated with the catheter to obtain a spatial curve equation of the catheter. In some embodiments, coordinates of point(s) at a front end of the curve may reflect position point information of the front end of the catheter, and a slope of the front end of the curve may reflect direction information of the front end of the catheter.

In some embodiments, the first point (or the second point) may be any point on the outline of the catheter or inside the catheter in the first real-time image (or the second real-time image), which is not limited in the present disclosure.

In 430, the processing device 120 (e.g., the indication module 330) may direct a display device (e.g., the terminal device 130 or a display device thereof) to configure a virtual object corresponding to the catheter in a reference image based on the spatial position information associated with the catheter.

In some embodiments, the reference image may be an image of the subject acquired or determined offline. For example, the reference image may be an image acquired or determined a certain time (e.g., 5 minutes ago, 10 minutes ago, 20 minutes ago, 1 hour ago, 5 hours ago, one day ago, two days ago) before an examination, a surgery, or a treatment. In some embodiments, the reference image may also be an image acquired in real-time during the procedure of the examination, the surgery, or the treatment. In some embodiments, the reference image and the real-time image may be obtained by the same acquisition device, or may be obtained by different acquisition devices.

In some embodiments, the reference image may be an image obtained by the acquisition device 110 (e.g., a 3D DSA device). In some embodiments, the reference image may be a reconstructed image obtained by the processing device 120 by performing an image reconstruction based on acquired image data (e.g., CT data). In some embodiments, the reference image may be a three-dimensional image or a four-dimensional image.

In some embodiments, the virtual object may include a virtual catheter (or a virtual guide wire). For example, the indication module 330 may configure a continuously changing virtual catheter in the reference image based on the spatial position information (e.g., the position and/or the orientation of the front end of the catheter) to visually present a simulated object corresponding to the catheter moving in the subject. In some embodiments, the virtual object may include a catheter marker (e.g., a cone marker) for directing the position and/or the orientation of the front end of the catheter.

In some embodiments, the virtual object may include a virtual endoscope. For example, the indication module 330 may configure the virtual endoscope in the reference image (e.g., a three-dimensional image) of the subject based on the spatial position information associated with the catheter, for example, the position and/or the orientation of the virtual endoscope may be configured to coincide with the position and/or the orientation of the front end of the catheter Further, the indication module 330 may direct the virtual endoscope to follow the moving of the catheter during the procedure of the examination, the surgery, or the treatment based on real-time spatial position information of the catheter. Correspondingly, a view angle or a visual field of the visual endoscope can reflect surrounding situation of the catheter in real-time during the examination, the surgery, or the treatment, so as to provide accurate reference information for a user (e.g., a doctor) during the procedure of the examination, the surgery, or the treatment.

Figure 7:
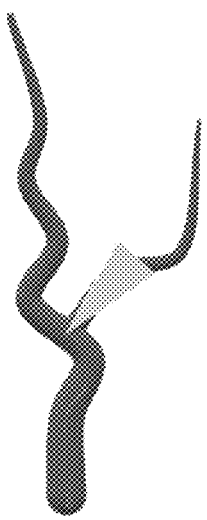
FIG. 7 is a schematic diagram illustrating an exemplary position or orientation of a virtual object corresponding to a catheter according to some embodiments of the present disclosure.

Merely by way of example, as shown in FIG. 7, the position and the orientation of the virtual endoscope may be configured to coincide with the position and the orientation of the front end of the catheter. Accordingly, the view angle or the visual field (or virtual images captured by the virtual endoscope) of the virtual endoscope can provide an intuitive reference for a user (e.g., a doctor). Specifically, the view angle or the visual field (or virtual images captured by the virtual endoscope) of the virtual endoscope may show a distribution of subjects (e.g., vessels) in front of the catheter during the moving of the catheter (or the front end of the catheter). The user (e.g., the doctor) can determine whether it is necessary to adjust the position and/or the orientation of the catheter (or the front end of the catheter) based on the view angle or the visual field (or virtual images captured by the virtual endoscope) of the virtual endoscope to control the catheter to continue to move along a desired path.

In some embodiments, before directing the display device to configure the virtual object corresponding to the catheter in the reference image, the processing device 120 may register the reference image with the acquisition device (e.g., the acquisition device 110) corresponding to the at least one real-time image, and then configure the virtual object in the registered reference image based on the spatial position information of the catheter. In some embodiments, "registration" may refer to adjusting a coordinate system of the reference image to coincide or substantially coincide with a coordinate system of the acquisition device (or the at least one real-time image).

In some embodiments, the at least one real-time image and the reference image may be obtained by the same acquisition device. Accordingly, there is a corresponding spatial relationship between the coordinate system of the at least one real-time image, the coordinate system of the reference image, and the coordinate system of the acquisition device. Accordingly, according to the spatial relationship, a spatial relationship between a real-time image acquired under any gantry angle and the reference image may be determined to realize the registration.

In some embodiments, the at least one real-time image and the reference image may be obtained by different acquisition devices. Accordingly, the coordinate system of the at least one real-time image, the coordinate system of the reference image, and the coordinate system of the acquisition device may be adjusted to be consistent based on a registration algorithm. Exemplary registration algorithms may include mean absolute difference algorithm, absolute error sum algorithm, error sum of squares algorithm, sequential similarity detection algorithm, local gray value coding algorithm, scale-invariant feature transformation method, Walsh transform method, wavelet transform method, etc.

In some embodiments, during an operation (e.g., an examination, a surgery, a treatment) associated with the subject, the processing device 120 may determine whether a motion (e.g., a rigid motion of a patient, a respiratory motion with a relatively large amplitude) associated with the subject occurs based on the at least one real-time image. In response to determining that a motion associated with the subject occurs during the operation, the processing device 120 may provide a notification (e.g., a voice reminder, a text reminder, an image reminder). In some embodiments, the motion associated with the subject may refer to any motion that may affect the catheter navigation.

For example, in a vascular interventional procedure, if the patient moves (causing a change in a position and/or an orientation of the vessel(s)), the processing device 120 may notify the user (e.g., the doctor) that a re-registration may be needed, or that a new reference image may need to be acquired to ensure the accuracy of catheter navigation.

In some embodiments, the processing device 120 may detect the motion associated with the subject by using Artificial Intelligence (AI) technology. For example, the processing device 120 may process at least two real-time images acquired at different time points through a trained image recognition model to identify whether the patient has moved (and/or a motion amplitude) during the operation. In some embodiments, an input of the trained image recognition model may include at least two real-time images of the subject acquired at different time points, and an output of the trained image recognition model may indicate whether a motion associated with the subject occurs (e.g., "1" for occurrence, "0" for non-occurrence) and/or an amplitude of the motion. In some embodiments, the trained image recognition model may be obtained by training an initial model based on a plurality of training samples. Each of the plurality of training samples may include a group of sample images as an input of the initial model and an occurrence result and/or a value of motion amplitude as a label. In some embodiments, the trained image recognition model may include a deep learning model, a recurrent neural network model, a convolution neural network model, etc.

In some embodiments, the processing device 120 may also determine an amplitude and/or a duration of the motion and provide a corresponding notification. In some embodiments, different amplitude levels and/or different duration levels may be predefined and correspond to different types of notifications. In some embodiments, the different types of notifications may indicate different strengths of notifications or reminders. For example, an amplitude and/or a duration with a relatively low level may correspond to a notification with a relatively low strength; an amplitude and/or a duration with a relatively high level may correspond to a notification with a relatively high strength.

Merely by way of example, take the "amplitude" as an example, the amplitude levels may include "small," "medium," and "large." In response to determining that the amplitude level of the motion is "small," the processing device 120 may provide a notification notifying "waiting for a moment" or "pause for a moment." In response to determining that the amplitude level of the motion is "medium," the processing device 120 may provide a notification notifying that a re-registration may be needed. In response to determining that the amplitude level of the motion is "large," the processing device 120 may provide a notification notifying that a new reference image may need to be acquired.

As another example, take the "amplitude" as an example, in response to determining that the amplitude level of the motion is "small," the processing device 120 may provide a voice notification with a relatively low volume or a text notification with a normal size font. In response to determining that the amplitude level of the motion is "medium," the processing device 120 may provide a voice notification with a medium volume or a text notification with a medium size font or with a normal color (e.g., blue, purple). In response to determining that the amplitude level of the motion is "large," the processing device 120 may provide a voice notification with a relatively high volume or a text notification with a relatively large size font or with a highlight color (e.g., red).

In some embodiments, during the procedure of the catheter navigation, the processing device 120 may dynamically determine whether a subject (e.g., a vessel) satisfies a preset condition, and dynamically control the acquisition process of the at least one real-time image based on the determination result. For example, the processing device 120 may dynamically control on/off of the acquisition units in the acquisition device (e.g., the acquisition device 110) corresponding to the at least one real-time image based on a surrounding situation of the subject to balance radiation dose and positioning accuracy. More descriptions may be found elsewhere in the present disclosure (e.g., FIG. 8 and descriptions thereof).

It should be noted that the above description is merely provided for the purposes of illustration, and not intended to limit the scope of the present disclosure. For persons having ordinary skills in the art, plurality of variations or modifications may be made under the teachings of the present disclosure. However, those variations and modifications do not depart from the scope of the present disclosure. For example, one or more other optional operations (e.g., a storing operation, a transmitting operation) may be added elsewhere in the process 400. In the storing operation, the processing device 120 may store information and/or data (e.g., the image data) associated with the catheter navigation in a storage device disclosed elsewhere in the present disclosure. In the transmitting operation, the processing device 120 may transmit information and/or data to the terminal device 130. As another example, operation 420 and operation 430 may be combined into a single operation.

Figure 8:
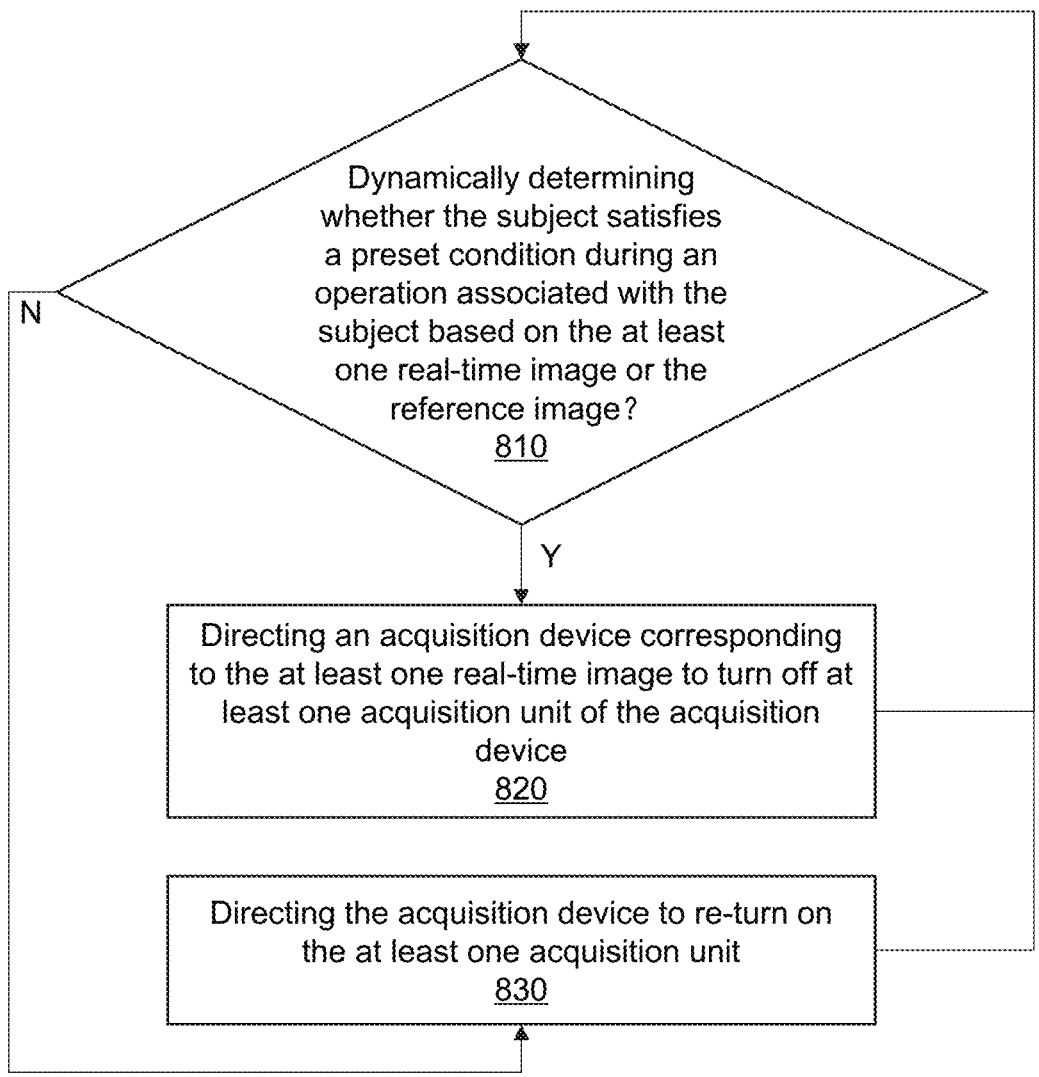
FIG. 8 is a flowchart illustrating an exemplary process for dynamically controlling on/off of acquisition units operating in an acquisition device according to some embodiments of the present disclosure.

FIG. 8 is a flowchart illustrating an exemplary process for dynamically controlling on/off of acquisition units operating in an acquisition device according to some embodiments of the present disclosure. In some embodiments, the process 800 may be executed by the medical system 100. For example, the process 800 may be implemented as a set of instructions stored in a storage device. In some embodiments, the processing device 120 (e.g., the processor 210 of the computing device 200 and/or one or more modules illustrated in FIG. 3) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 810, the processing device 120 (e.g., the indication module 330) may dynamically determine whether the subject satisfies a preset condition during an operation (e.g., an examination, a surgery, a treatment) associated with the subject based on the at least one real-time image or the reference image.

In some embodiments, the preset condition may be related to a distribution of subjects near (e.g., within a predetermined range) the catheter (or the front end of the catheter). For example, taking the subject being a vessel as an example, the preset condition may be a count, a density, an intersection degree, a complexity, etc. of vessels near the front end of the catheter.

In some embodiments, the distribution of subjects may be determined based on an image recognition process. Specifically, still taking a vessel as an example, since the vessel is a tube structure, the processing device 120 may extract multiple slices of the vessel and determine center points of the multiple slices. Further, the processing device 120 may determine a path by linking the multiple center points and determine the path as a center path of the vessel. The center path may reflect a distribution situation of the vessel and/or surrounding vessel(s). For example, if there is a bifurcation or an overlap on the center path, it may indicate that there is a bifurcation or an overlap on the vessel.

In some embodiments, the processing device 120 may determine the distribution of subjects through a machine learning model. In some embodiments, an input of the machine learning model may include real-time images or reference images of the subject, and an output of the machine learning model may indicate a distribution (e.g., a distribution map of vessels) of subjects. In some embodiments, the machine learning model may be obtained by training an initial model based on a plurality of training samples. Each of the plurality of training samples may include a sample image as an input of the initial model and a sample distribution (e.g., a distribution diagram) of subjects in the sample image as a label. In some embodiments, the machine learning model may include a deep learning model, a recurrent neural network model, a convolution neural network model, etc.

In response to determining that the subject satisfies the preset condition during the operation, in 820, the processing device 120 may control the acquisition device corresponding to the at least one real-time image to turn off at least one acquisition unit of the acquisition device. For example, in response to determining that the distribution of subjects is relatively simple during operation, indicating that an accurate positioning of the catheter can be achieved without multiple real-time images (e.g., real-time images acquired under multiple acquisition angles), the processing device 120 may turn off at least a portion of the acquisition units to reduce radiation dose.

In response to determining that the subject does not satisfy the preset condition during the operation, in 830, the processing device 120 may control the acquisition device to re-turn on at least one acquisition unit. For example, in response to determining that the distribution of subjects is relatively complex during the operation, indicating that multiple real-time images (e.g., real-time images acquired under multiple acquisition angles) need to be acquired to ensure the positioning accuracy of the catheter, the processing device 120 may re-turn on at least a portion of the previously turned off acquisition unit(s).

Figure 9A:
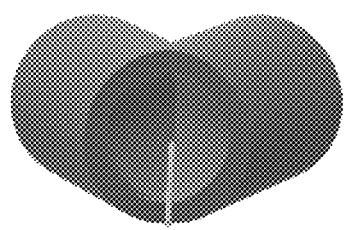
FIG. 9A and FIG. 9B are schematic diagrams illustrating exemplary view angles or view fields of a virtual endoscope under different vessel distributions according to some embodiments of the present disclosure.
Figure 9B:
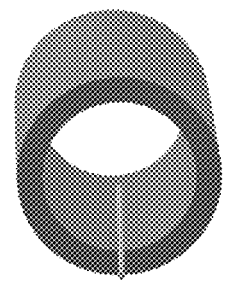

Merely by way of example, as shown in FIG. 9A and FIG. 9B, taking an operation (e.g., an examination, a surgery, a treatment) of a vessel as an example, it is assumed that the acquisition device 110 is a double-C vascular machine used to acquire images of vessels. At the beginning of the operation (e.g., when the catheter has just entered the vessel), the processing device 120 may turn on the double C-vascular machine (that is, turn on both the two acquisition units thereof) and acquire two real-time images acquired under two different acquisition angles to determine initial positioning information of the catheter. As the catheter moves along the vessel, as shown in FIG. 9A, when the distribution of the vessels near the catheter (or the front end of catheter) is relatively simple (e.g., no bifurcations and no overlaps), —for example, during the procedure from the femoral artery to the coronary artery of the heart, during the procedure from the femoral artery to the abdominal aorta to the thoracic aorta, —the processing device 120 may turn off one acquisition unit of the double-C vascular machine (i.e., only one acquisition unit is turned on). In this situation, only one real-time image acquired by one acquisition unit can achieve an accurate positioning of the catheter, accordingly, turning off one acquisition unit can reduce radiation dose. Further, as shown in FIG. 9B, when the distribution of the vessels near the catheter (or the front end of the catheter) is relatively complex (e.g., there are bifurcations or overlaps), —for example, when the catheter moves to bifurcations of the abdominal artery or intersections of multiple vessels, —the processing device 120 may re-turn on the previously turned off acquisition unit to acquire two real-time images under two different acquisition angels to ensure the positioning accuracy of the catheter.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for catheter navigation, comprising:
at least one storage medium including a set of instructions; and
at least one processor in communication with the at least one storage medium, wherein when executing the set of instructions, the at least one processor is directed to cause the system to perform operations including:
obtaining at least one real-time image associated with a subject, the at least one real-time image including a catheter at least partially inside the subject;
determining spatial position information associated with the catheter based on the at least one real-time image;
directing a display device to configure a virtual object corresponding to the catheter in a reference image associated with the subject based on the spatial position information;
determining whether the subject satisfies a preset condition during an operation associated with the subject based on the at least one real-time image or the reference image, the preset condition being related to a distribution of the subject within a predetermined range of a front end of the catheter, wherein the subject is a vessel and the preset condition is that a distribution of the vessel within the predetermined range of the front end of the catheter presents vessel bifurcation or vessel overlapping; and
in response to determining that the subject satisfies the preset condition during the operation, directing an acquisition device corresponding to the at least one real-time image to turn off at least a part of the acquisition device, the at least a part of the acquisition device is configured to obtain an image, and keep a remaining part of the acquisition device on, the remaining part of the acquisition device is configured to obtain an image.

2. The system of claim 1, wherein the at least one real-time image is obtained by the acquisition device, the acquisition device including a double C-arm acquisition device.

3. The system of claim 1, wherein the at least one real-time image at least includes a first real-time image acquired under a first acquisition angle and a second real-time image acquired under a second acquisition angle.

4. The system of claim 3, wherein the determining spatial position information associated with the catheter based on the at least one real-time image includes:
determining a first point associated with the catheter in the first real-time image;
determining a first line based on the first point and a first reference point associated with the acquisition of the first real-time image;
determining a second point associated with the catheter in the second real-time image;
determining a second line based on the second point and a second reference point associated with the acquisition of the second real-time image; and
determining the spatial position information associated with the catheter based on the first line and the second line.

5. The system of claim 1, wherein the spatial position information associated with the catheter includes at least one of position point information of the catheter or direction information of the catheter.

6. The system of claim 1, wherein
the at least one real-time image includes at least one two-dimensional image associated with the subject; and
the reference image includes a three-dimensional image associated with the subject.

7. The system of claim 1, wherein the directing a display device to configure a virtual object corresponding to the catheter in a reference image associated with the subject based on the spatial position information includes:
registering the reference image with the acquisition device corresponding to the at least one real-time image; and
directing the display device to configure the virtual object corresponding to the catheter in the registered reference image based on the spatial position information.

8. The system of claim 1, wherein the directing a display device to configure a virtual object corresponding to the catheter in a reference image associated with the subject based on the spatial position information includes:
in response to determining that the subject does not satisfy the preset condition during the operation, directing the acquisition device to re-turn on the at least a part of the acquisition device.

9. The system of claim 1, wherein the directing a display device to configure a virtual object corresponding to the catheter in a reference image associated with the subject based on the spatial position information includes:
determining whether a motion associated with the subject occurs during the operation associated with the subject based on the at least real-time image; and
in response to determining that a motion associated with the subject occurs during the operation, providing a notification.

10. The system of claim 1, wherein the distribution of the subject is determined by a machine learning model, and to determine the distribution of the subject, the at least one processor is directed to cause the system to perform operations including:
inputting the at least one real-time image or the reference image of the subject into the machine learning model, and
outputting, by the machine learning model, the distribution of the subject.

11. The system of claim 1, wherein
the spatial position information associated with the catheter includes a position and an orientation of the front end of the catheter;
the virtual object corresponding to the catheter includes a virtual endoscope; and
a position and an orientation of the virtual endoscope are configured to coincide with the position and the orientation of the front end of the catheter and direct the virtual endoscope to follow movement of the catheter.

12. A method for catheter navigation, comprising:
- obtaining at least one real-time image associated with a subject, the at least one real-time image including a catheter at least partially inside the subject;
- determining spatial position information associated with the catheter based on the at least one real-time image;
- directing a display device to configure a virtual object corresponding to the catheter in a reference image associated with the subject based on the spatial position information;
- determining whether the subject satisfies a preset condition during an operation associated with the subject based on the at least one real-time image or the reference image, the preset condition being related to a distribution of the subject within a predetermined range of a front end of the catheter, wherein the subject is a vessel and the preset condition is that a distribution of the vessel within the predetermined range of the front end of the catheter presents vessel bifurcation or vessel overlapping; and
- in response to determining that the subject satisfies the preset condition during the operation, directing an acquisition device corresponding to the at least one real-time image to turn off at least a part of the acquisition device, the at least a part of the acquisition device is configured to obtain an image, and keep a remaining part of the acquisition device on, the remaining part of the acquisition device is configured to obtain an image.

13. The method of claim 12, wherein the at least one real-time image at least includes a first real-time image acquired under a first acquisition angle and a second real-time image acquired under a second acquisition angle.

14. The method of claim 13, wherein the determining spatial position information associated with the catheter based on the at least one real-time image includes:
- determining a first point associated with the catheter in the first real-time image;
- determining a first line based on the first point and a first reference point associated with the acquisition of the first real-time image;
- determining a second point associated with the catheter in the second real-time image;
- determining a second line based on the second point and a second reference point associated with the acquisition of the second real-time image; and
- determining the spatial position information associated with the catheter based on the first line and the second line.

15. The method of claim 12, wherein
- the at least one real-time image includes at least one two-dimensional image associated with the subject; and
- the reference image includes a three-dimensional image associated with the subject.

16. The method of claim 12, wherein the directing a display device to configure a virtual object corresponding to the catheter in a reference image associated with the subject based on the spatial position information includes:
- registering the reference image with the acquisition device corresponding to the at least one real-time image; and
- directing the display device to configure the virtual object corresponding to the catheter in the registered reference image based on the spatial position information.

17. The method of claim 12, wherein the directing a display device to configure a virtual object corresponding to the catheter in a reference image associated with the subject based on the spatial position information includes:
- in response to determining that the subject does not satisfy the preset condition during the operation, directing the acquisition device to re-turn on the at least a part of the acquisition device.

18. The method of claim 12, wherein the directing a display device to configure a virtual object corresponding to the catheter in a reference image associated with the subject based on the spatial position information includes:
- determining whether a motion associated with the subject occurs during the operation associated with the subject based on the at least real-time image; and
- in response to determining that a motion associated with the subject occurs during the operation, providing a notification.

19. A non-transitory computer readable medium, comprising executable instructions that, when executed by at least one processor, direct the at least one processor to perform a method, the method comprising:
- obtaining at least one real-time image associated with a subject, the at least one real-time image including a catheter at least partially inside the subject;
- determining spatial position information associated with the catheter based on the at least one real-time image;
- directing a display device to configure a virtual object corresponding to the catheter in a reference image associated with the subject based on the spatial position information;
- determining whether the subject satisfies a preset condition during an operation associated with the subject based on the at least one real-time image or the reference image, the preset condition being related to a distribution of the subject within a predetermined range of a front end of the catheter, wherein the subject is a vessel and the preset condition is that a distribution of the vessel within the predetermined range of the front end of the catheter presents vessel bifurcation or vessel overlapping; and
- in response to determining that the subject satisfies the preset condition during the operation, directing an acquisition device corresponding to the at least one real-time image to turn off at least a part of the acquisition device, the at least a part of the acquisition device is configured to obtain an image, and keep a remaining part of the acquisition device on, the remaining part of the acquisition device is configured to obtain an image.

* * * * *